United States Patent [19]

Innis

[11] Patent Number: 5,142,033

[45] Date of Patent: Aug. 25, 1992

[54] STRUCTURE-INDEPENDENT DNA AMPLIFICATION BY THE POLYMERASE CHAIN REACTION

[75] Inventor: Michael A. Innis, Moraga, Calif.

[73] Assignee: Hoffmann-La Roche Inc., Nutley, N.J.

[21] Appl. No.: 738,324

[22] Filed: Jul. 31, 1991

Related U.S. Application Data

[63] Continuation of Ser. No. 248,556, Sep. 23, 1988, Pat. No. 5,091,310.

[51] Int. Cl.⁵ .................. C07H 21/04; C12Q 1/68; C12P 19/34
[52] U.S. Cl. .......................... 536/27; 435/6; 435/15; 435/91; 435/183; 435/810; 436/501; 436/808; 536/28; 536/29; 530/350; 530/820; 935/16; 935/17; 935/18; 935/78; 935/88
[58] Field of Search .................. 435/6, 91, 15, 810, 435/183; 436/501, 808; 536/27-29; 935/16, 17, 18, 78, 88; 530/820, 350

[56] References Cited

U.S. PATENT DOCUMENTS

| 4,683,195 | 7/1987 | Mullis et al. | 435/6 |
| 4,683,202 | 7/1987 | Mullis | 435/91 |
| 4,795,699 | 1/1989 | Tabor et al. | 435/5 |
| 4,921,794 | 5/1990 | Tabor et al. | 435/91 |

FOREIGN PATENT DOCUMENTS 0237362 9/1987 European Pat. Off. .
0258017 3/1988 European Pat. Off. .

OTHER PUBLICATIONS

Barr et al., 1986, Bio Techniques 4(5):428-432.
Saiki et al., 1988, Science 239:476-491.
Promega advertisement and certificated of analysis dated Aug. 9, 1988 "Tag Track Sequencing System".
Heiner et al., 1988, Preliminary Draft.
McConlogue et al., 1988, Nuc. Acids Res. 16(20):9869.
Innis et al., 1988, Proc. Natl. Acad. Sci. USA 85:9436-9440.
Mizusawa et al., 1986, Nuc. Acids Res. 14(3):1319-1324.
Simpson et al., 1988 Biochem. and Biophys. Res. Comm. 151(1):487-492.
Chait, 1988, Nature 333:477-478.

*Primary Examiner*—Margaret Moskowitz
*Assistant Examiner*—Ardin H. Marschel
*Attorney, Agent, or Firm*—Kevin R. Kaster; Stacey R. Sias

[57] ABSTRACT

Structure-independent amplification of DNA by the polymerase chain reaction can be achieved by incorporation of 7-deaza-2'-deoxyguanosine-5'-triphosphate into the amplified DNA.

9 Claims, 2 Drawing Sheets

STRUCTURE-INDEPENDENT DNA AMPLIFICATION BY THE POLYMERASE CHAIN REACTION

This application is a continuation of application Ser. No. 07/248,556, filed Sept. 23, 1988, now U.S. Pat. No. 5,091,310.

BACKGROUND OF THE INVENTION

1. Field of the Invention

The present invention relates to a process for amplifying a specific segment of nucleic acid. Methods for amplifying nucleic acid can be used to facilitate the cloning of DNA and the characterization of both DNA and RNA sequences and so are useful methods for purposes of recombinant DNA technology and the study of molecular biology. In addition, the amplification of specific nucleic acid segments greatly facilitates the detection of pathogens and of disease states associated with the presence of particular nucleic acid sequences, so the present invention is also of importance in medical diagnostic procedures. The detection of specific nucleic acid sequences is also useful for purposes of forensic medicine and paternity and individuality determination.

2. Description of Related Disclosures

U.S. Pat. No. 4,683,202 discloses a process for amplifying a specific nucleic acid segment by the polymerase chain reaction (PCR). PCR involves the use of two oligonucleotide primers, an agent for polymerization, a target nucleic acid template, and successive cycles of denaturation of nucleic acid and annealing and extension of the primers to produce a large number of copies of a particular nucleic acid segment. The segment copied consists of a specific sequence of nucleotides from the target template. This specific sequence is defined by regions on the template that can hybridize to the primers and the nucleic acid sequence between those regions. PCR methodology has had a profound impact in the fields of molecular biology, recombinant DNA technology, forensic medicine, and medical diagnostic technology.

U.S. Pat. No. 4,683,195 discloses a variety of methods for using PCR to amplify and then detect or clone a given nucleic acid segment. European Patent Publication No. 237,362 further illustrates the utility of PCR in the detection of specific nucleic acid sequences by disclosing that PCR can be used in conjunction with labeled probes and "dot-blot" methodology to detect the presence of a nucleic acid sequence initially present in extraordinarily small amounts.

Methods for performing PCR are disclosed in Ser. No. 063,647, filed Jun. 17, 1987, which issued as U.S. Pat. No. 4,965,188, and which is a continuation-in-part (CIP) of Ser. No. 899,513, filed Aug. 22, 1986, now abandoned, which is a CIP of Ser. No. 828,144, filed Feb. 7, 1986, which issued as U.S. Pat. No. 4,683,195, and which is a CIP of Ser. No. 791,308, filed Oct. 25, 1985, which issued as U.S. Pat. No. 4,683,202, and which is a CIP of abandoned Ser. No. 716,975, filed Mar. 28, 1985, all of which are incorporated herein by reference.

European Patent Publication No. 258,017 discloses a thermostable DNA polymerase that significantly simplifies PCR methodology. PCR involves successive rounds of denaturation or "melting" of double-stranded nucleic acid. The denaturation process is often carried out by heating the sample of nucleic acid, although a nucleic acid helicase can also be used for this purpose. However, this heating process can destroy the activity of the agent for polymerization, typically a DNA polymerase, that is used in PCR. Consequently, DNA polymerase must be added to PCR reaction mixtures after each heat-denaturation step unless a thermostable polymerase is employed. European Patent Publication No. 258,017 discloses a number of such thermostable polymerases, of which the polymerase from *Thermus aquaticus*, Taq polymerase, is most preferred for use in PCR, because the enzyme can survive repeated cycles of heating and cooling in PCR.

Saiki et al., Jan. 19, 1988, *Science* 239:487–491, describe methods for using Taq polymerase in PCR. Saiki et al. also describe the amplification of a specific DNA segment present only once in a sample of $10^5$ to $10^6$ cells.

Methods for purifying Taq polymerase and for the recombinant expression of the enzyme are disclosed in Ser. No. 143,441, now abandoned, filed Jan. 12, 1988, which is a CIP of Ser. No. 063,509, filed Jun. 17, 1987, which issued as U.S. Pat. No. 4,889,818, which is a CIP Ser. No. 899,241, now abandoned, filed Aug. 22, 1986, each of which is incorporated herein by reference.

Instruments for performing automated PCR are disclosed in Ser. No. 899,061, filed Aug. 22, 1986, which is a CIP of Ser. No. 833,368, filed Feb. 25, 1986, now abandoned. Structure-independent amplification of DNA can also be useful in the DNA sequencing methods disclosed in Ser. No. 249,367, filed Sep. 23, 1988. The present invention can be applied in the generation of single-stranded DNA by the method termed "asymmetric PCR" disclosed in Ser. No. 248,896, filed Sep. 23, 1988. The disclosures of these related patents and applications are incorporated herein by reference.

PCR methodologies offer enormous practical advantages over any other known way to amplify nucleic acid sequences. On occasion, however, a given pair of PCR primers does not yield an amplification product, even though the target sequence is present in the reaction mixture. When faced with such a "no amplification" result, the practitioner must do extensive testing of reagents and operating techniques to determine the origin of the problem. Sometimes such testing reveals the cause of the problem to be the particular primers used in the amplification, because primers that hybridize to another region of the target sequence can provide efficient amplification. This problem of "no amplification" occurs infrequently but, prior to the present invention, unpredictably. The problem is compounded by the difficulty in determining whether the primers are the reason for the inefficient amplification results.

Scientists working in areas not involving the polymerase chain reaction have observed that certain nucleic acid sequences can form stable secondary structures, such as palindromic hairpin loops or compressed regions. Because the presence of such structures can lead to anomalous migration patterns during gel electrophoresis, i.e., as in DNA sequencing, researchers attempted to find means for preventing the formation of secondary structures in nucleic acids. Barr et al., 1986, *Bio Techniques* 4(5):528–532, reported that use of 7-deaza-2'-deoxyguanosine-5'-triphosphate ($c^7dGTP$) in dideoxy-sequencing reaction mixtures helped to to resolve abnormal and compressed regions in the sequencing gels.

The present invention results from a synthesis of these two arts and provides a method for structure-independent amplification of DNA by PCR.

SUMMARY OF THE INVENTION

The present invention provides a method for structure-independent amplification of DNA by the polymerase chain reaction. The method comprises:

(a) treating the DNA under hybridizing conditions with a pair of oligonucleotide primers, an agent for polymerization, deoxyadenosine-5'-triphosphate, (dATP), deoxycytosine-5'-triphosphate (dCTP), thymidine-5'-triphosphate (TTP), and $c^7dGTP$ such that an extension product of each oligonucleotide primer is formed that is complementary to the DNA, wherein the extension product of a first primer of said primer pair, when separated from its template, can serve as a template for synthesis of the extension product of a second primer of said pair;

(b) separating the extension products from the templates on which the extension products were synthesized; and (c) repeating steps (a) and (b) on the extension products produced in step (b).

DETAILED DESCRIPTION OF THE INVENTION

Figure 1:
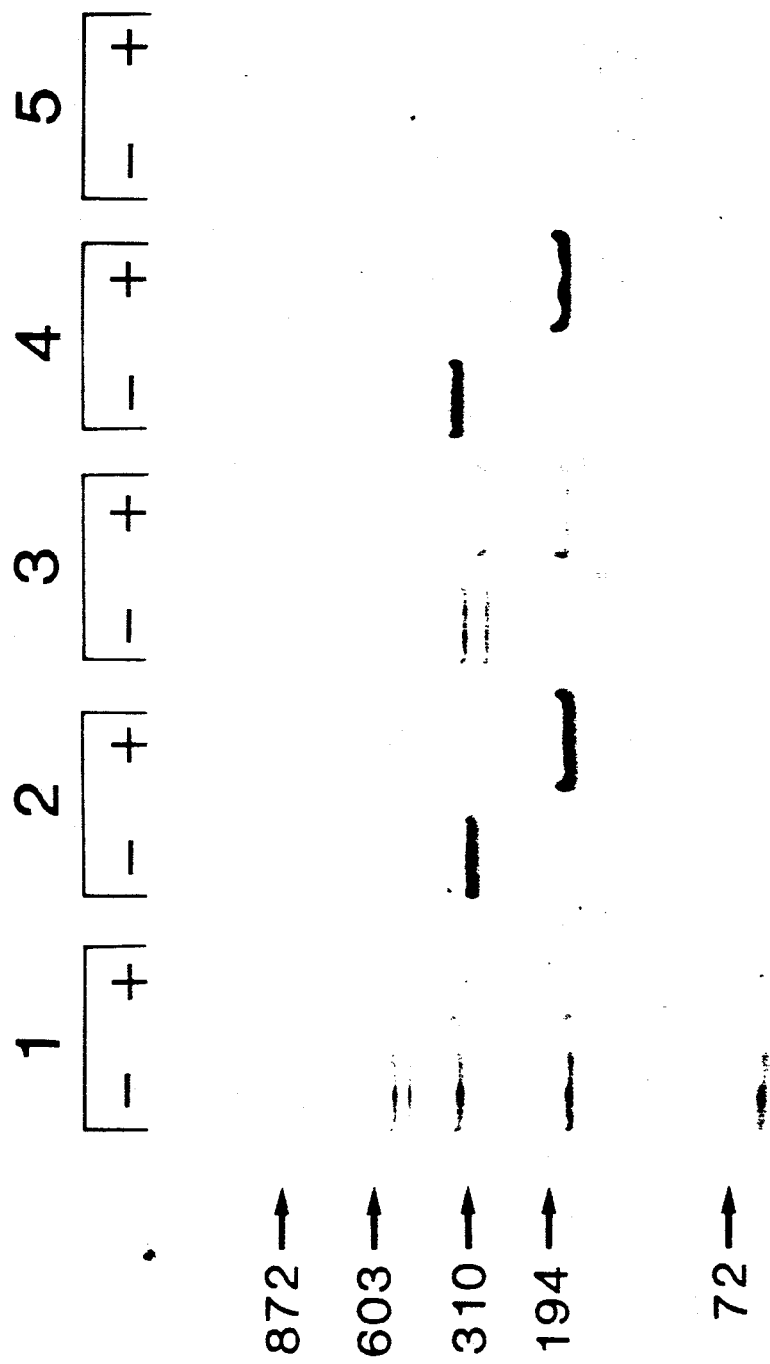
FIG. 1 is a picture of the gel produced by the procedure described in Example 1.

The present invention provides a method for structure-independent amplification of DNA by the polymerase chain reaction (PCR). The polymerase chain reaction, described in U.S. Pat. Nos. 4,683,195 and 4,683,202, essentially involves repeated cycles of denaturing double-stranded DNA, annealing primers to the denatured DNA, and extending the primers. The primers are oriented so that extension of either primer produces a template to which the other primer can bind and be extended in turn. Each round of denaturing of DNA and annealing and extending of primers doubles the amount of that segment of DNA defined by the two primers.

The present inventor recognized that the presence of secondary structure in single-stranded DNA can greatly reduce the efficiency of amplification in the PCR process. Secondary structure in a single-stranded DNA molecule involves the ability of complementary residues, such as those found in palindromic sequences, to form hairpin-like structures, also known as "stem-and-loops" or "hairpin loops". High guanosine (G) and cytosine (C) content in a nucleic acid sequence can lead to compression of that sequence through Hoogsteen bond formation. In addition, researchers involved with sequencing nucleic acids have observed band compressions and other abnormal gel migrations with DNA segments containing apparently normal base composition. The present inventor believes the presence of secondary structure including compressions and hairpins, can significantly inhibit either the annealing and/or extending of the oligonucleotide primers used in the PCR process.

Prior to the present invention, the only way known to get certain DNA segments to amplify required testing a number of different primer pairs flanking the region of interest until one pair yielded amplification. An unrecognized cause for the difficulty of amplification of these sequences was the presence of secondary structure in the single strand copies of the target segment preventing priming (annealing of primers to template) and extending of the primers.

The present invention provides a simple method for overcoming this unrecognized problem. This method for structure-independent amplification of DNA comprises:

(a) treating the DNA under hybridizing conditions with a pair of oligonucleotide primers, an agent for polymerization, dATP, dCTP, TTP, and 7-deaza-2'-deoxyguanosine-5'-triphosphate ($c^7dGTP$) such that an extension product of each oligonucleotide primer is formed that is complementary to the DNA, wherein the extension product of a first primer of said primer pair, when separated from its template, can serve as a template for synthesis of the extension product of a second primer of said pair;

(b) separating the extension products from the templates on which the extension products were synthesized; and (c) repeating steps (a) and (b) on the extension products produced in step (b).

The utilization of $c^7dGTP$ in a polymerase chain reaction results in the incorporation of 7-deazaguanine into the amplified DNA produced in the reaction. The structure destabilizing base analog 7-deazaguanine precludes Hoogsteen bond formation by virtue of replacement of the N-7 of the guanine ring with a methine moiety. 7-deazaguanine does not impair Watson-Crick base pairing as does inosine, another structure-destabilizing base analog. Utilization of inosine in PCR results in frequent mismatching of bases during primer extension.

Utilization of $c^7dGTP$ in PCR, however, results in an astounding increase in the specificity of PCR on nucleic acid templates that contain secondary structure and/or compressed regions. This benefit provided by the present invention is clearly illustrated by the results described in Examples 1 and 2, below. PCR reactions performed with $c^7dGTP$ but without dGTP are typically less efficient than PCR reactions performed with mixtures of $c^7dGTP$ and dGTP. The optimal mixture is believed to be about 3:1 $c^7dGTP$ and dGTP, respectively.

The method of the invention is illustrated below by an example of the PCR amplification of genomic DNA that codes for the 5'-untranslated leader of murine ornithine decarboxylase (ODC) mRNA. This DNA is very G and C rich (75% G+C) and predicted to be able to form very stable hairpin-like, stem-and-loop structures (−93 kcal). Standard PCR reactions, without $c^7dGTP$, resulted in no detectable amplification of this segment. However, the segment can be efficiently and specifically amplified by the method of the present invention.

PCR is usually performed on genomic or recombinant DNA, but the process can be used to amplify any nucleic acid segment. For instance, RNA can be amplified by PCR simply by first making a cDNA copy of the RNA using a primer and reverse transcriptase. The primer can even be one of the members of the primer pair used in the PCR process. This amplification primer pair is added to the cDNA, either before or after cDNA synthesis, and PCR is carried out. After the first round of PCR, in which the cDNA is essentially made into a double-stranded DNA by the extension of one primer of the pair, the amplification process is identical to that of any double-stranded DNA. This aspect of the method of the invention is described in more detail in Example 2.

The agent for polymerization used in the PCR process to extend the primers in a template-dependent reaction is usually a DNA polymerase. The preferred polymerase for use in PCR is the DNA polymerase of *Thermus aquaticus*, commercially available from Perkin-Elmer Cetus. *T. aquaticus* DNA polymerase is known as Taq polymerase; recombinant Taq polymerase produced in an *E. coli* or other host cell can also be used for PCR. However, DNA polymerases such as T4 DNA polymerase, T7 DNA polymerase, *E. coli* DNA polymerase I, or the Klenow fragment of *E. coli* DNA polymerase I can also be used in PCR. Taq polymerase is preferred because of the high annealing and reaction temperatures possible when using Taq polymerase for PCR. Taq polymerase is very processive in the temperature ranges of 55°–80° C. High temperatures can destabilize secondary structure in nucleic acids.

Denaturation of the primer extension products from their templates can be easily accomplished by heat denaturation of the DNA. However, enzymatic or other means can also be used to denature the DNA for purposes of the present invention. For instance, a helicase could be used to denature the DNA.

Primers are oligonucleotides, usually deoxyribonucleotides several nucleotides in length, that can be extended in a template-specific manner by the polymerase chain reaction. The nucleoside-5'-triphosphates utilized in the extension process, typically dATP, dCTP, dGTP, and TTP, are each present in a concentration typically ranging from 10 mM to 1.5 mM during the extension reaction.

Those skilled in the art recognize that the present method can be used in a variety of contexts where amplification of DNA is desired. The following Examples are provided merely to illustrate the invention and not to limit the scope of the accompanying claims.

EXAMPLE 1

Structure-Independent Amplification of DNA

Genomic DNA encoding the 5'-untranslated leader of murine ODC mRNA was isolated for use in the amplification reaction. The deoxyribonucleotide primers used in the reaction are depicted below.

LM30 5'-ATGAATTCTGCGTCTCCATGACGACGTGCTCG

LM31 5'-TAGAATTCGCACATCCCTCCCGCGTCCCG

Each 50 μL PCR reaction mixture contained 0.36 μg of genomic DNA, 10 pmol of each primer, 1.25 units of Taq DNA polymerase (Perkin-Elmer/Cetus), 200 μM dATP, 200 μM dCTP, 200 μM TTP, 50 mM KCl, 10 mM tris (pH=8.4), 2.5 mM MgCl$_2$, 200 μg/mL gelatin, and dGTP and/or c$^7$dGTP as described below. Each reaction was overlaid with several drops of mineral oil to prevent evaporation/condensation. PCR was carried out using a Perkin-Elmer/Cetus Instruments Thermal Cycler. The thermocycle profile was 30 seconds at 94° C., one minute at 55° C., and one minute at 72° C. The cycle was repeated 30 times for each sample, except as noted.

Five different amplification reactions were performed using varying amounts of dGTP and c$^7$dGTP:

(1) 30 cycles with 200 μM dGTP;
(2) 30 cycles with 200 μM c$^7$dGTP followed by 30 cycles with 100 μM c$^7$dGTP and 100 μM dGTP;
(3) 30 cycles with 100 μM dGTP and 100 μM c$^7$dGTP;
(4) 30 cycles with 50 μM dGTP and 150 μM and c$^7$dGTP;
(5) 30 cycles with 200 μM c$^7$dGTP.

The amplification product was expected to be 310 bp in size. The products of the amplification were examined by electrophoresing a portion of the reaction mixture on a polyacrylamide gel, staining the gel with ethidium bromide, and viewing the gel under an ultraviolet light. FIG. 1 is a picture of the UV-exposed gel. Reaction numbers are indicated over the appropriate lanes. Another portion of the reaction mixture was digested with restriction enzyme TaqI, expected to cleave the 310 bp amplification product, and the TaqI-digested samples were electrophoresed on the same gel. TaqI-cleaved products are designated by a (+) in FIG. 1.

Reaction 1, standard PCR containing no c$^7$dGTP, gave no detectable amplification of the desired product but produced a number of extraneous bands. The remaining reactions, all of which contained varying amounts of c$^7$dGTP, each contained some specific (TaqI-cleavable) 310 bp reaction product. Reaction 3, which contained 100 μM dGTP and 100 μM c$^7$dGTP, also contained extraneous amplification products. Reactions 2, 4, and 5 produced only the expected 310 bp product as determined by the gel analysis. Reaction 5, which contained no dGTP, did not produce as much of the 310 bp amplification product as did Reactions 2 and 4. The product of Reaction 2 was cloned, and independent clones were sequenced using the Sanger dideoxynucleotide sequencing method. No sequence errors were observed in the cloned product.

EXAMPLE 2

Amplification of Beta-Actin mRNa by PCR Using 7-deazaguanine

The nucleic acid sequence of the human beta-actin mRNA was deduced from the cDNA sequence by Ponte et al., 1984, *Nucleic Acids Research* 12:1687–1696. The primers used in the amplification, EK 169 and EK 170, are depicted below:

EK 169  5' GAT GAT GAT ATC GCC GCG CTC
EK 170  5' CAT GTC GTC CCA GTT GGT GAC

K562 cells were used as a source of mRNA for the amplification. The mRNA prepared was first used to make cDNA using reverse transcriptase. The reverse transcriptase reactions were carried out in 20 μL of 1X PCR buffer (50 mM KCl; 20 mM Tris-Cl, pH=8.4; 2.5 mM MgCl$_2$; and 100 μg/mL BSA) containing 1 μg of K562 cell cytoplasmic RNA, 1 unit/mL RNAsin (Promega Biotec), 1 mM dATP, 1 mM CTP, 1 mM TTP, 10 pmol of EK170, 200 units of reverse transcriptase (Bethesda Research Laboratories), and either 1 mM dGTP or 0.75 mM c$^7$dGTP and 0.25 mM dGTP. Thus, when deazaguanine was used, dGTP was replaced with a 3:1 mixture of c$^7$dGTP:dGTP. Samples were incubated for 30 minutes at 42° C.

After the reverse transcriptase reaction, the reverse transcriptase was heat-inactivated by placing the reaction vessel in a 95° C. water bath for 5 minutes. The reaction mixture was then diluted 5-fold by the addition of 80 μL of 1X PCR buffer containing 10 pmol of primer EK 169 and 1 unit of Taq polymerase. PCR was carried out for 40 cycles; each cycle consisted of a 20 second denaturation step at 95° C., a 20 second annealing of primers step at 55° C., and a 1 minute primer extension step at 72° C. After PCR was complete, 5 μL of the reaction mixture were analyzed on 2% NuSieve/1% ME-agarose gels using TEA buffer and ethidium staining. A picture of this gel is presented in FIG. 2 of the accompanying drawings. Lane 1 shows the 123 bp ladder (marketed by Bethesda Research Laboratories). Lanes 2 and 3 each contain 5 μL of the amplification reaction mixture that contained $c^7dGTP$ and clearly show the presence of the expected 243 bp product. Lanes 4 and 5 each contain 5 μL of the amplification reaction mixture that contained only dGTP and show no expected product but show a substantial amount of extraneous product.

Figure 2:
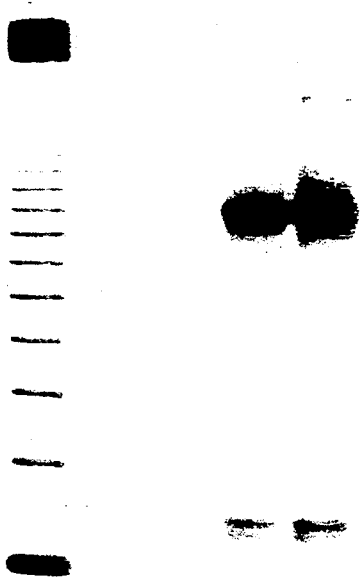
FIG. 2 is a picture of the gel produced by the procedure described in Example 2.

As illustrated in FIG. 2, PCR without $c^7dGTP$ on beta-actin mRNA using the EK 169 and EK 170 primer pair did not result in detectable amplification of actin sequences. However, inclusion of $c^7dGTP$ in the PCR reaction mixture gave amplified PCR product of the expected size. The 7-deazaguanine helped to destabilize secondary structure in the amplified DNA and allowed amplification of the actin sequence. Thus, utilization of $c^7dGTP$ in PCR improves the reliability of amplification of sequences with high GC content and/or other secondary structure. This structure-independent amplification method is especially important in areas such as diagnostics, forensics, and molecular biology.

Other modifications of the embodiments of the invention described above that are obvious to those of ordinary skill in the areas of molecular biology, medical diagnostic technology, biochemistry and related disciplines are intended to be within the scope of the accompanying claims.

We claim:

1. A double-stranded DNA having 7-deazaguanine in both strands composition comprising an amplified nucleic acid sequence produced by:

(a) treating a sample containing a nucleic acid segment to be amplified under hybridizing conditions with two oligonucleotide primers, a DNA polymerase, dATP, dCTP, TTP, and $c^7dGTP$ such that an extension product of each oligonucleotide primer is formed that is complementary to a strand of said nucleic acid segment, wherein the extension product synthesized from each primer, when separated from its complement, can serve as a template for synthesis of the extension product of the other primer;

(b) separating the primer extension products from the templates on which they were synthesized to produce single-stranded molecules; and (c) treating the product of step (b) with oligonucleotide primers such that a primer extension product is synthesized using each of the single strands produced in step (b) as a template, resulting in amplification of the nucleic acid sequence.

2. The composition of claim 1, wherein at step (a) dGTP is also present.

3. A kit for structure-independent amplification of DNA by the polymerase chain reaction, said kit comprising:

(a) dATP, dCTP, TTP, and $c^7dGTP$; and
   (b) a thermostable DNA polymerase.

4. The kit of claim 3, further comprising dGTP.

5. The kit of claim 4, wherein said dGTP and said $c^7dGTP$ are in a solution and said dGTP and said $c^7dGTP$ are present at a ratio of 1:3 dGTP:$c^7dGTP$.

6. The kit of claim 3, wherein the DNA polymerase is *Thermus aquaticus* DNA polymerase.

7. The kit of claim 4, wherein the DNA polymerase is *Thermus aquaticus* DNA polymerase.

8. The kit of claim 5, wherein the DNA polymerase is *Thermus aquaticus* DNA polymerase.

9. The kit of claim 8, further comprising a pair of oligonucleotide primers.

* * * * *